US012583285B2

(12) United States Patent (10) Patent No.: US 12,583,285 B2

D'Angelo (45) Date of Patent: Mar. 24, 2026

(54) METHOD TO CONTROL AN AIR CONDITIONING SYSTEM IN A PASSENGER COMPARTMENT OF A ROAD VEHICLE

(71) Applicant: FERRARI S.p.A., Modena (IT)

(72) Inventor: Enrico D'Angelo, Modena (IT)

(73) Assignee: FERRARI S.P.A., Modena (IT)

(*) Notice: Subject to any disclaimer, the term of this patent is extended or adjusted under 35 U.S.C. 154(b) by 801 days.

(21) Appl. No.: 17/173,771

(22) Filed: Feb. 11, 2021

(65) Prior Publication Data

US 2021/0245574 A1 Aug. 12, 2021

(30) Foreign Application Priority Data

Feb. 11, 2020 (IT) ........................ 102020000002665

(51) Int. Cl.
B60H 1/00 (2006.01)
G06V 20/59 (2022.01)
(Continued)

(52) U.S. Cl.
CPC ..... B60H 1/00742 (2013.01); B60H 1/00828 (2013.01); B60H 1/00871 (2013.01);
(Continued)

(58) Field of Classification Search
CPC ............ B60H 1/00742; B60H 1/00828; B60H 1/00871; B60H 1/00892; G06V 20/59;
(Continued)

(56) References Cited

U.S. PATENT DOCUMENTS

2006/0259219 A1* 11/2006 Wakiyama ............. B60H 1/005
701/36
2013/0144470 A1* 6/2013 Ricci ..................... G06F 3/0482
701/2
(Continued)

FOREIGN PATENT DOCUMENTS

CN 202764652 U 3/2013
CN 103303096 A 9/2013
(Continued)

OTHER PUBLICATIONS

Jacobs et al., Metabolic and Heart Rate Responses to Open-Wheel Automobile Road Racing: A Single-Subject Study, 2000, Journal of Strength and Conditioning Research, 14(2), 157-161 (Year: 2000).*
(Continued)

*Primary Examiner* — Anne Marie Antonucci

(74) *Attorney, Agent, or Firm* — CANTOR COLBURN LLP

(57) ABSTRACT

A method and apparatus to control an air conditioning system in a passenger compartment of a road vehicle comprising the steps of detecting a body temperature of at least a part of the body of one or more occupants of the passenger compartment and transmitting the detected body temperature to the air conditioning system, which controls a plurality of ventilation devices arranged inside the passenger compartment. The method comprises the further steps of identifying the number and the position of the one or more occupants seated in the passenger compartment; determining an optimized tuning at least based on the body temperature detected by the sensor member and controlling the ventilation devices as a function of the optimized tuning.

14 Claims, 2 Drawing Sheets

(51) Int. Cl.
  *H04N 23/23*  (2023.01)
  *A61B 5/00*  (2006.01)
  *A61B 5/01*  (2006.01)

(52) U.S. Cl.
  CPC ......... *B60H 1/00892* (2013.01); *G06V 20/59*
    (2022.01); *H04N 23/23* (2023.01); *A61B 5/01*
    (2013.01); *A61B 5/6893* (2013.01); *A61B*
    *2503/12* (2013.01)

(58) Field of Classification Search
  CPC ..... A61B 5/01; A61B 5/6893; A61B 2503/12;
    H04N 5/33
  See application file for complete search history.

(56) References Cited

U.S. PATENT DOCUMENTS

| | | | |
|---|---|---|---|
| 2016/0363340 A1* | 12/2016 | Shikii | ...................... F24F 11/74 |
| 2018/0001734 A1* | 1/2018 | Faust | ................. B60H 1/00742 |
| 2018/0244129 A1 | 8/2018 | Whitens et al. | |

FOREIGN PATENT DOCUMENTS

| | | |
|---|---|---|
| CN | 203358278 U | 12/2013 |
| CN | 106080092 A | 11/2016 |
| CN | 108473020 A | 8/2018 |
| DE | 102016215058 A1 | 2/2018 |
| JP | H06344755 A | 12/1994 |
| JP | H0725219 A | 1/1995 |
| JP | H10197348 A | 7/1998 |
| JP | 2004142567 A | 5/2004 |
| JP | 2005047457 A | 2/2005 |
| JP | 2005138767 A | 6/2005 |
| JP | 2005145327 A | 6/2005 |
| JP | 2006027557 A | 2/2006 |
| JP | 2006232007 A | 9/2006 |
| JP | 2007308096 A | 11/2007 |
| JP | 2017032268 A | 2/2017 |
| JP | 2017128242 A | 7/2017 |
| WO | 2016029044 A1 | 2/2016 |
| WO | 2016070047 A1 | 5/2016 |

OTHER PUBLICATIONS

Search Report issued in Italian Patent Application No. 202000002665 completed Oct. 26, 2020; 8 pages.
Extended European Search Report for Patent Application No. 21156486.9 mailed Mar. 23, 2021, 10 pages.
Japanese Office Action for Japanese Patent Application No. 2021-018979 dated Jan. 28, 2025.
Chinese Office Action for Chinese Patent Application No. 202110184699.1 dated Nov. 29, 2024.
Chinese Office Action for the corresponding Chinese Application No. 202110184699.1, Date of Mailing: May 23, 2025; English translation, 6 pages.
Search Report for the corresponding Chinese Application No. 2021101846991; 2 pages.

\* cited by examiner

METHOD TO CONTROL AN AIR CONDITIONING SYSTEM IN A PASSENGER COMPARTMENT OF A ROAD VEHICLE

CROSS-REFERENCE TO RELATED APPLICATIONS

This patent application claims priority from Italian patent application no. 102020000002665 filed on Feb. 11, 2020, the entire disclosure of which is incorporated herein by reference.

TECHNICAL FIELD

The present invention relates to a method to control an air conditioning system in a passenger compartment of a road vehicle.

PRIOR ART

Modern road vehicles are substantially always equipped with an air conditioning system which allows adjusting (increasing, decreasing or keeping constant) the temperature inside the vehicle (i.e. a passenger compartment). By way of example, the air conditioning system is frequently used during the summer season to lower the temperature on the inside of the passenger compartment with respect to the temperature on the outside of the vehicle; conversely, during the winter season, the air conditioning system is generally used to heat the inside of the passenger compartment so as to have a higher temperature with respect to the outside.

An air conditioning system normally comprises a plurality of ventilation devices (comprising the so-called air "nozzles") arranged in different positions on the inside of the passenger compartment of the road vehicle. For example, the ventilation devices can be divided by types based on the zone toward which they direct an air flow and can be independently adjusted and/or selectively activated.

Modern air conditioning systems have ample possibilities for adjusting the modalities with which the temperature on the inside of the passenger compartment is adjusted. For example, by operating each ventilation device in a completely independent manner, it is possible to manually increase or decrease the flow rate (i.e. the intensity) and/or the direction of the air flow emitted by each ventilation device.

Moreover, automatic (both single-zone and two-zone) air conditioning systems are more and more common, which adjust the intensity and the temperature of the air based on an inside temperature detected by one or more thermometers arranged on the inside of the passenger compartment (for example, under a seat, inside a dashboard or a console). This inside temperature is usually used for a closed-loop (feedback) control which adjusts the temperature and the intensity of the air flow flowing out of the ventilation devices, so as to reach the temperature set manually by one (or two, in the case of a two-zone system) of the occupants.

However, these ample adjustment possibilities are simply based on reaching the set temperature on the inside of the passenger compartment, without actually considering the real thermal conditions, the real presence and the actual position of the occupants of the passenger compartment of the road vehicle. For these reasons, generally, the desired manually set temperature is periodically modified by the driver or by a passenger so as to adapt said desired inside temperature to the immediate needs of those seated inside the vehicle.

For example, in the systems of the prior art, by setting a certain desired temperature value, the air conditioning system works to reach such average temperature on the inside of the passenger compartment, without considering the needs and the habits of the occupants and without evaluating what incidence the solar irradiation has in the temperature distribution on the inside of the passenger compartment of the road vehicle.

DESCRIPTION OF THE INVENTION

The object of the present invention, among others, is to provide a method for controlling an air conditioning system in a passenger compartment of a road vehicle, which control method allows improving (optimizing) the climatic perception on the inside of the passenger compartment by one or more occupants and, at the same time, is easily and immediately usable for all the users and does not distract the driver from driving.

According to the present invention, a method for controlling an air conditioning system in a passenger compartment of a road vehicle is provided, according to what claimed by the appended claims.

The claims describe preferred embodiments of the present invention constituting an integral part of the present description.

BRIEF DESCRIPTION OF THE DRAWINGS

The present invention will now be described with reference to the accompanying drawings, which illustrate a non-limiting embodiment example thereof, wherein.

PREFERRED EMBODIMENTS OF THE INVENTION

Figure 1:
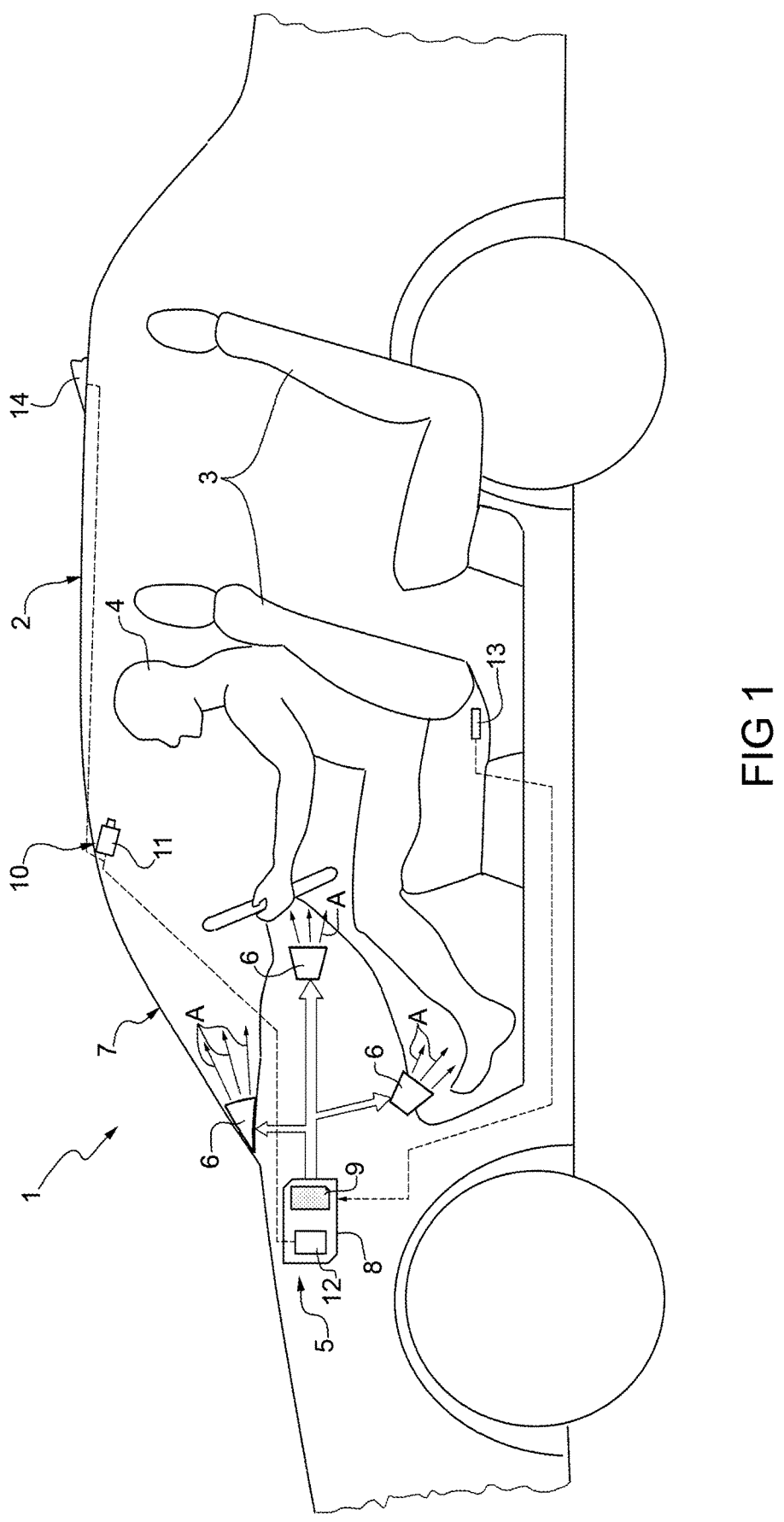
FIG. 1 is a schematic and side view of a road vehicle equipped with an air conditioning system which is controlled according to the control method of the present invention.

In FIG. 1, reference numeral 1 indicates, as a whole, a road vehicle (in particular a car) provided with two front driven (i.e. not driving) wheels and two rear driving wheels. In a front position, an internal combustion engine is arranged, which produces a torque which is transmitted to the driving wheels via a transmission.

The road vehicle 1 comprises a passenger compartment 2 which is provided with two or more seats 3 each adapted to accommodate a corresponding occupant 4; i.e. in the passenger compartment 2 a driver is always seated, with the addition of possible passengers (whose presence is obviously optional).

The road vehicle 1 comprises an air conditioning system 5 which allows letting inside the passenger compartment 2 a plurality of air flows A in the passenger compartment 2. The air flows A can be both hot air flows (previously heated by means of resistors or by transmission of the heat of the endothermic engine), and cold air flows (by transmission of the heat with the evaporator). The terms "hot" and "cold" are respectively intended to mean hotter and colder with respect to an existing temperature on the inside of the vehicle 1.

In the non-limiting embodiment of FIG. 1, the air conditioning system 5 comprises a plurality of ventilation devices 6 arranged inside the passenger compartment 2 of the road vehicle 1 and through which the air flows A let in by the air conditioning system 5 transit inside the passenger compartment 2. In particular, the ventilation devices 6 are divided into three different categories based on the zone toward which such devices 6 direct the air flows A. For example, the air conditioning system 5 comprises at least one ventilation device 6 for the defrosting (defrost), in which the respective air flow A is directed toward or along a windshield 7; at least one ventilation device 6 for the ventilation (vent) of the occupants 4, in which the respective air flow A is directed toward the body of the occupants 4; and at least one bottom device (down) directing the respective air flow A toward the feet of the occupants 4.

In some non-limiting cases, the ventilation devices 6 are further divided based on the side of the vehicle on which they are positioned (for example, right side, left side and/or front side, rear side).

The air conditioning system 5 further comprises a control unit 8, which is configured to control the ventilation devices 6. In particular, the control unit 8 determines the flow rate of the air flows A and the temperature of the same when flowing out of the ventilation devices 6 (i.e. from the nozzles).

Advantageously but not necessarily, the air conditioning system 5 (in particular the control unit 8) comprises a memory 9 inside which the adjustment parameters are saved. More specifically, such adjustment parameters are saved so as to keep track of the preferences of the occupants 4.

Advantageously, the control system 5 comprises at least one sensor member 10 configured to identify at least the number and the position (for example on which seat they are seated) of the occupants 4 inside the passenger compartment 2.

Advantageously but not necessarily, the sensor member 10 comprises (in particular, is) a thermal camera 11 configured to frame one or more occupants 4 of the passenger compartment 2 and determine the temperature of at least a part of the body of at least one occupant 4. In some non-limiting cases, the thermal camera 11 communicates the data detected to the control unit 8. In other non-limiting cases, the thermal camera 11 communicates the data detected to a suitable image processing system, which is connected to the control unit 8.

According to some non-limiting embodiments, the thermal camera 11 is arranged at a ceiling light of the passenger compartment 2 (as illustrated in FIG. 1). In particular, the thermal camera 11 is arranged in a central portion (above the rear-view mirror).

According to other non-limiting embodiments, the thermal camera 11 is arranged at a pillar of the passenger compartment 2. In particular, the thermal camera 11 is arranged in an upper portion of a pillar arranged between the base of a frame and the ceiling of the passenger compartment 2.

In some non-limiting cases, especially in the case of a two-seater vehicle, the air conditioning system 5 comprises two thermal cameras 11, one facing the driver and one facing the passenger.

In other non-limiting cases, especially in the case of a vehicle provided with back seats 3, the air conditioning system 5 comprises at least three thermal cameras 11, of which one facing the driver, one facing the passenger and one facing the back seats 3.

According to the non-limiting embodiment of FIG. 1, the air conditioning system 5 comprises at least one thermometer 13 arranged inside the passenger compartment 2. In particular, the thermometer 13 is arranged in a position difficult to be accessed by the occupants 4 such as, for example, the inside of a central dashboard or the lower part of a seat 3.

Advantageously but not necessarily, the air conditioning system 5 also comprises an irradiation sensor 14, which is configured to determine the direction and the intensity of the solar radiations with respect to the vehicle 1. In particular, the irradiation sensor 14 communicates the data detected to the control unit 8.

The control system 5 further comprises a processing device 12, which determines an optimized tuning based on the detection of the sensor member 10 and controls the ventilation devices 6 based on the optimized tuning.

According to a further aspect of the present invention, a method for controlling the air conditioning system 5 is provided.

The control method comprises the step of detecting, by means of the sensor member 10, a body temperature of at least a part of the body of an occupant 4 of the passenger compartment 2; and the step of providing (i.e. communicating) such detected body temperature to the air conditioning system 5, in particular to the calculation unit 8.

Advantageously, the method comprises the further step of identifying the number and the position of the occupants 4 inside the passenger compartment 2. More specifically, during this step which of the seats 3 are actually occupied by an occupant 4 is defined.

Additionally, the method comprises a step of determining an optimized tuning at least based on the body temperature detected by the sensor member, and controlling the ventilation devices 6 accordingly (i.e. as a function of the optimized tuning).

Advantageously but not necessarily, the optimized tuning changes depending on the driving style of an occupant (i.e. of the driver of the vehicle 1), which is determined based on the data detected, in particular, by means of an inertial measuring unit (known per se and not illustrated). The driving style of the driver is defined based on, at least, the longitudinal acceleration ($A_L$ in FIG. 4), the lateral or transverse acceleration ($A_T$ in FIG. 4) and the speed. Such parameters are processed according to known models which determine a driving value by calculating a weighted average of the aforementioned measurements and comparing it with reference parameters.

Advantageously but not necessarily, the optimized tuning changes upon the variation of the at least one body temperature of a part of the body of at least one of the occupants 4 of the passenger compartment 2.

Advantageously but not necessarily, the sensor device 10, i.e. the thermal camera 11, frames at least one occupant 4 so as to view the upper portion of the body thereof (in other words, anything above the waist of the occupant 4).

Figures 2, 3:
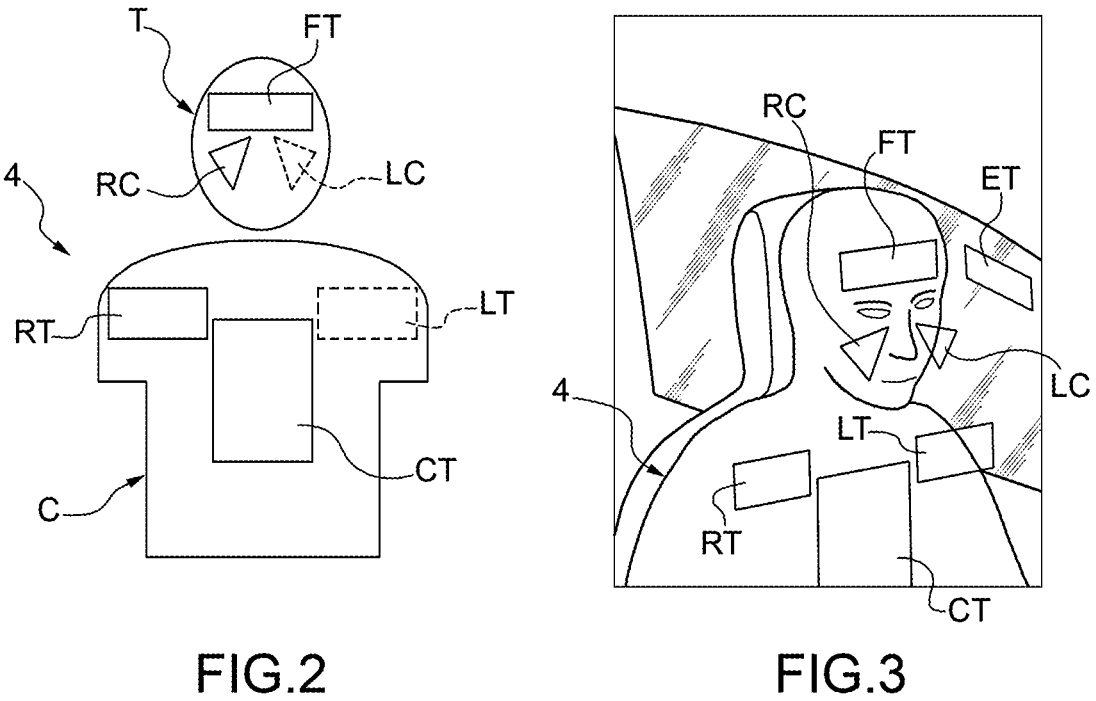
FIG. 2 illustrates schematically and frontally a division into thermal areas of the bust of an occupant of the passenger compartment.
FIG. 3 is a perspective and schematic view of the field of vision of a sensor member inside the passenger compartment.

The non-limiting embodiment of FIG. 2 illustrates schematically a division of the upper portion of an occupant 4. In particular, according to such division, the thermal camera 11 detects a plurality of different temperatures relating to the framed occupant 4. More specifically, the thermal camera 11 calculates an average of the temperature of a certain part of the body of the occupant 4, providing a scalar value to the control unit 8 relating to that part of the body.

In the non-limiting embodiment of FIG. 2, the upper portion of an occupant 4 is schematically divided macroscopically into head T and trunk C.

Preferably, in relation to the head T, a forehead temperature FT is detected. Specifically, also temperatures RC and LC of the right cheek and of the left cheek of the occupant, respectively, are detected.

Advantageously but not necessarily, in relation to the trunk C, a chest and/or abdomen temperature CT is detected. Specifically, also temperatures RT and LT of the right and of the left of the occupant, respectively, are detected. The temperatures RT and LT are the temperatures of the shoulders and/or of the right and left arms of the occupant 4 framed by the thermal camera 11.

Advantageously but not necessarily, the optimized tuning changes depending on the build of at least one of the occupants 4. The term "build" is intended to mean the body type of the occupant 4.

Figure 4:
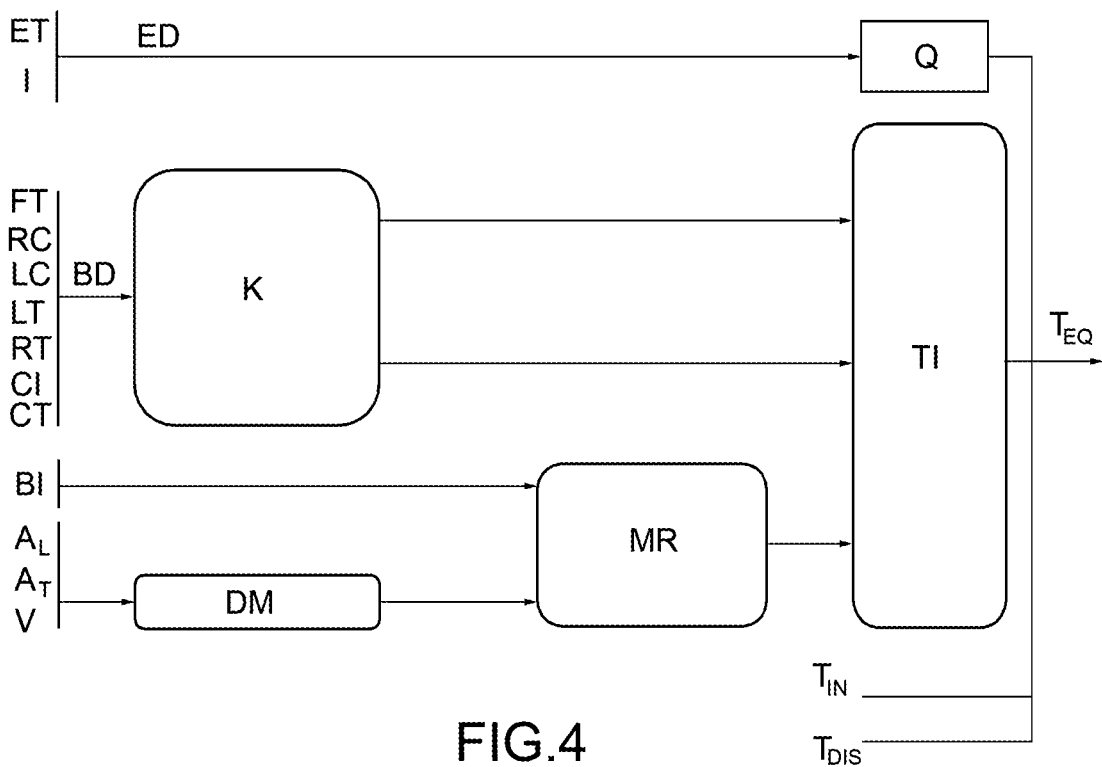
FIG. 4 illustrates a possible flowchart for determining a thermal index.

According to some non-limiting embodiments, the build of the occupant 4 is determined by means of the thermal camera 11. In particular, the build is identified in terms of a body index BI (as indicated in FIG. 4). Such body index BI is obtained by outlining the images obtained from the thermal camera 11 to determine the dimensions of the body of the occupant 4. Alternatively or additionally, the body index BI takes into consideration the weight of the occupant 11 (detected, for example, with a load sensor comprised in a seat 3).

Advantageously but not necessarily, the optimized tuning changes depending on the clothes worn by the occupant 4 of the vehicle 1 (FIG. 3), for example by the driver. In particular, via the thermal camera 11, a clothing index CI (FIG. 4) is determined which determines the thermal insulation of the occupant 4 due to the clothes and with respect to the temperature inside the passenger compartment.

Advantageously but not necessarily, the clothes of the occupants 4 are determined based on a difference between the body temperature of a part of the body covered by the clothes and the body temperature of an uncovered part of the body.

According to some non-limiting embodiments, the clothing index CI is determined based on the difference between the head temperature T (in particular the forehead temperature FT) of the occupant 4 and the trunk temperature C (in particular the chest and/or abdomen temperature CT).

Advantageously but not necessarily, the optimized tuning changes depending on the gender of the occupant 4.

In some non-limiting cases, the gender of the occupant is determined as a function of a personal opening key used to open the vehicle 1, or by means of a voice recognition system present on board the vehicle 1, or by means of a driving style or by means of the weight detected by the seat 3. In such manner, it is possible to customize the optimized tuning of the air conditioning system 5 so that, in the case in which the occupant is a man, the temperature of the air flowing out of the ventilation devices 6 is slightly lower (or higher) with respect to the case in which the occupant is a woman. In particular, the air conditioning system 5 can adjust in such sense, and in a differentiated manner, a two-zone, three-zone or four-zone air conditioning.

According to some non-limiting embodiments, the optimized tuning changes depending on the head temperature T (for example FT). The head T is generally the part of the body with the greatest temperature variability or in any case the part from which it is easier to understand the thermal state of an occupant 4 (for example, whether said occupant is hot or cold). In such manner, at the increase of the head temperature T, it is possible to reduce the average temperature inside the passenger compartment accordingly because it would mean that the occupant 4 is getting hot (this is obviously also valid in the converse case).

Advantageously but not necessarily, the optimized tuning changes based on the irradiation I (FIG. 4) of the road vehicle 1.

According to some non-limiting embodiments, the value of the irradiation I of the road vehicle 1 is processed (by the control unit 8) based on the difference between the body temperature RT of a right part of the body and the body temperature LT of a left part of the body of at least one of the occupants 4 and detected using the thermal camera 11.

Alternatively or additionally, the value of the irradiation I of the road vehicle 1 is processed taking into account the detection of the irradiation sensor 14 installed on board the vehicle 1.

Advantageously but not necessarily, the optimized tuning changes depending on the temperature ET on the outside of the passenger compartment 2.

According to some non-limiting embodiments such as the one illustrated in FIG. 3, the temperature ET on the outside of the passenger compartment 2 is processed based on the temperature of at least one window, detected by means of the thermal camera 11 arranged inside the passenger compartment 2.

Alternatively or additionally, the temperature ET on the outside of the passenger compartment 2 is processed taking into account the detection of a thermometer on the outside of the passenger compartment (arranged, for example, in the lower part of the body of the vehicle 1).

Advantageously but not necessarily, the method comprises the further steps of detecting a temperature on the inside of the passenger compartment 2 by means of at least the thermometer 13 (arranged inside the passenger compartment 2) and refining the optimized tuning based on the inside temperature detected by the thermometer 13.

In some non-limiting cases, the control method comprises the step of setting (only once, i.e. not continuously in a cyclical manner) a desired temperature by means of an interface device, known per se and thus not illustrated (for example, a push-button panel, a voice command, a wheel, etc.). This step is preferably performed by an occupant 4 of the vehicle 1, for example a driver, who sets a desired temperature that he or she considers consistent with his or her habits and with the existing temperature perception inside the passenger compartment (i.e. if said occupant is hot or cold). In particular, the method further provides a comparison of the temperature on the inside of the passenger compartment 2 with the desired set temperature and refining the optimized tuning based on a difference between the temperature on the inside of the passenger compartment 2 and the desired temperature.

Advantageously but not necessarily, the method for controlling the air conditioning system 5 comprises the further step of adjusting a flow rate and/or a temperature of the air flows A flowing out of the plurality of ventilation devices 6 arranged inside the passenger compartment 2. In particular, the temperature and the flow rate of the air flows A are adjusted independently of one another. More specifically, the temperature and the flow rate of the air flows A are adjusted independently between the different ventilation devices 6. This way, it is possible to increase the comfort of the occupants 4 of the vehicle taking into account all the considerations set out above. For example, if the solar irradiation predominantly hits one side of the vehicle 1, the ventilation devices 6 arranged on that side will emit an air flow A at a lower temperature with respect to the air flow emitted at the same moment by the ventilation devices 6 arranged on the side in the shade of the vehicle 1 (i.e. the side opposite the one irradiated by the sun).

Advantageously but not necessarily, the optimized tuning changes depending on a thermal comfort index TI which takes into consideration part or all of the variables up to now described and detected.

In the non-limiting embodiment of FIG. 4, the thermal index TI is obtained by calculating a weighted average between: the outside data ED (relating to the outside temperature ET and the irradiation I); the body data BD (relating to the temperatures and/or the data FT, RC, LC, RT, LT, CT, CI detected or obtained by means of the images displayed by the thermal camera 11); the body index IB (relating to the build of the occupants 4) and the dynamic model DM (obtained as a function of the longitudinal and lateral accelerations $A_L$, $A_T$ and of the speed V of the vehicle 1).

In particular, as illustrated in FIG. 4, the data relating to the temperatures FT, RC, LC, RT, LT, CT detected by the thermal camera 11 generate a value K, which is used, together with a metabolic index MR obtained from the data of the dynamic model DM (depending on the driving style) and of the body index of the occupants 4, in order to process the thermal index IT. In order to obtain a detailed index MR, in addition to the body index BI, the type of driving is also taken into account.

In particular, following the studies of Schaudienst and Vogdt, the correlation between build and gender (possibly also physical condition, by evaluating the temperature of the abdomen—the fat is less permeated than the muscle—or the silhouette of the occupant) is used to calculate the related metabolic index MR.

According to some non-limiting embodiments, the value K already takes into account also the outside data ED. In particular, following the model of Hagino and Junichiro (known in the literature) which takes into account the relative importance (weight) of the local temperatures on the general thermal comfort index TI.

Advantageously but not necessarily, at least part of the (in particular all of the) data/values used for calculating the thermal index TI are each multiplied by a coefficient, so that the thermal index TI is a weighted average.

According to a non-limiting embodiment, the thermal index TI is expressed by the formula:

$$TI=[CI+k3(CR-CL)+k4(RT-LT)+MR]-Off$$

wherein:

$$CI=k_1(FT-O_1)-k_2(CT-O_2)$$

and $$MR=k_5(DM-O_5)+k_6(BI-O_6)$$

In particular, the coefficients $k_1$-$k_6$ and the offsets Off, $O_1$-$O_6$ are determined experimentally, by means of allocation tables which allow the allocation of a specific coefficient based on the desired weight of the variable multiplied by such coefficient and the performance of a calibration by means of the offsets which allows adapting the optimized tuning to different vehicle models. The sum of the coefficients $k_1$-$k_6$ is preferably equal to one.

Advantageously but not necessarily, the offset Off is a parameter used for setting a preference of the occupant 4 and saving it in the memory 9. In particular, if an occupant 4 has a certain thermal disposition, i.e. is on average hot or on average cold, the offset Off allows the system 5 to take into account the preference of said occupant and to change it as soon as the occupant 4 is recognized in accordance with one of the methods described in the foregoing.

As illustrated in the non-limiting embodiment of FIG. 4, the thermal index TI (which is also multiplied by a pre-defined weight) is added to the data ED relating to the outside of the vehicle 1 and the data relating to the inside of the vehicle, but not obtained from the thermal camera (i.e. the temperature $T_{IN}$ detected by means of the thermometer 13) on the inside of the passenger compartment 2 and the discharge temperature $T_{DIS}$ of the air flows A at the venti-lation devices 6 (more specifically at the nozzles).

According to a non-limiting embodiment, an equivalent (measured) temperature $T_{EQ}$ designed to determine the out-put temperature of the air flows A is expressed by the formula:

$$T_{EQ}=Q_1(T_{IN})+Q_2(T_{DIS}-\theta)+Q_3(T_E)+Q_4(I)+Q_5(TI)$$

wherein $T_{DIS}$ indicates the detected temperature of the air flows A flowing out of the ventilation devices 6 (i.e. it is an input of the system 5) and the temperature $\theta$ indicates the temperature to be set of the air flows A flowing out of the ventilation devices 6 (i.e. it is a feedback output of the system 5).

In particular, the coefficients $Q_1$-$Q_5$ are determined experimentally, by means of allocation tables which allow allocating a given coefficient based on the desired weight of the variable multiplied by such coefficient. The sum of the coefficients $Q_1$-$Q_5$ is preferably equal to one.

Specifically, the thermal index TI represents the additional component to the formula of the equivalent temperature $T_{EQ}$. In this non-limiting case, everything is maintained as an open-loop control, in which, at an increase of the thermal index TI, its equivalent temperature $T_{EQ}$ increases and thus the outflowing discharge temperature $\theta$ decreases, while, at the decrease of the thermal index, its equivalent temperature $T_{EQ}$ also decreases and thus the outflowing discharge tem-perature $\theta$ increases. In other non-limiting cases, the control is a closed-loop control in which the thermal index TI represents the feedback of f the equivalent temperature $T_{EQ}$.

Advantageously but not necessarily, the flow rate of the air flows A flowing out of the discharge devices 6 increases proportionally to the increase in the difference between the thermal index TI and the equivalent temperature $T_{EQ}$.

In use, an occupant 4 boarding the vehicle 1 defines a desired temperature signal by means of an interface device known per se and thus not illustrated.

The embodiments described herein can be combined with one another without departing from the protection scope of the present invention.

In use, the processing device 12 identifies, using, for example, the sensor member 10 or weight sensors arranged at the seats 3, the number and the position of the occupants 4 seated in the passenger compartment 2, determines an optimized tuning based on all the parameters described in the foregoing and as illustrated in FIG. 4, and thus controls (adjusts) the temperature and the flow rate of the air flows A flowing out of the ventilation devices 6 depending on the optimized tuning. Obviously, the optimized tuning changes upon the variation of the number and/or the position of the occupants 4 in the passenger compartment 2 and of the parameters described above; i.e. when the number and/or the position of the occupants 4 of the passenger compartment 2 modifies, when the outside data ED or the temperatures contained in the block K of FIG. 4 are modified, or when the occupants 4 change and the metabolic index MR is modified, also the optimized tuning must consequently be modified.

For example, if only the driver is present, then the thermal camera 11 will exclusively detect the body data and the temperatures relating solely to the driver and will adapt the air flows A so as to compensate possible variations in the outside (temperature, irradiation) or inside (clothing, diversified temperatures for different parts of the body, etc.) conditions.

Obviously, if both the driver and the front seat passenger (or also other passengers) are present, the ventilation devices 6 must be controlled taking into account the needs of both of occupants (detected, for example, by means of a plurality of thermal cameras 11) in order to optimize the climatic perception of both occupants without privileging (excessively) one at the expense of the other.

Obviously, if there is only a single thermal camera present in the vehicle, the same can frame a plurality of occupants 4. In the case in which there is a single-zone system and a plurality of occupants 4, the processing device 12 controls the ventilation devices so as to obtain a thermal condition which satisfies, at least partially, all occupants. In other words, the air conditioning system 5 is controlled so as to reach an average thermal condition with respect to the optimal needs of the occupants 4 of the passenger compartment 2.

Although the above-described invention makes particular reference to a very precise embodiment example, it is not to be considered limited to such embodiment example, all the variants, modifications or simplifications covered by the appended claims falling within its scope, such as, for example, a different type of sensors, a different type of vehicle, a different parametrization of the coefficients and of the offsets, etc.

The control method described above has numerous advantages.

First, the control method described above allows optimizing the control of an air conditioning system 5 as it has been observed that the perception of the temperature by the occupants 4 seated in the passenger compartment 2 is significantly influenced by the number, by the arrangement of the occupants 4, by the solar irradiation, by the clothing of the occupants, by their body type, etc. Moreover, the passenger compartment 2 has a small and complex (i.e. full of elements of different shapes) volume and the addition or the subtraction of a single occupant perceptibly modifies the thermal response of the passenger compartment 2.

Therefore, thanks to the control method described above, it is possible to provide, in particular when only the driver is present, or when the driver and a passenger are present (in the case of a two-zone system), a thermal condition which is simultaneously adaptive and customizable.

Obviously, when increasing the number of the occupants 4 of the passenger compartment 2, the customization and the adaptability of the system inevitably decreases having to accept compromises in favour of the passengers, but it is anyway possible to reach the best possible compromise in order to maximize the quality of the thermal comfort perceived by all occupants 4.

The control method described above functions in an entirely automatic manner, i.e. transparent with respect to the occupants 4, and can thus be used by anybody (not requiring any actions) without entailing any type of distraction while driving.

Finally, the control method described above does not entail any increase in costs: the processing device 12 can in fact be developed entirely via software in one of the existing control units or in the hardware of the air conditioning system 5, while the thermal camera 14, the irradiation sensor, the thermometer 13 and the weight sensors are already present in the passenger compartment 2 for other purposes.

LIST OF THE REFERENCE NUMERALS OF THE FIGURES

1 road vehicle
2 passenger compartment
3 seats
4 occupant/s
5 air conditioning system
6 ventilation device
7 windshield
8 memory
9 control unit
10 sensor member
11 thermal camera
12 processing device
13 thermometer
14 irradiation sensor
ED outside data
ET outside temperature
I irradiation
BI body index
$A_L$ longitudinal acceleration
$A_T$ lateral acceleration
V speed
DM dynamic model
MR metabolic index
T head
c trunk
FT forehead temperature
RC right cheek temperature
LC left cheek: temperature
CT chest and/or abdomen temperature
RT right temperature
LT left temperature
BD body data
CI clothing index
TI thermal index
$T_{IN}$ J inside temperature
$T_{DIS}$ discharge temperature
$T_{EQ}$ equivalent temperature

The invention claimed is:
1. A control method for controlling an air conditioning system in a passenger compartment of a road vehicle; the control method comprises the steps of:
detecting, by means of a sensor member, a body temperature of at least a part of the body of one or more occupants of the passenger compartment and
transmitting the detected body temperature to the air conditioning system, which controls a plurality of ventilation devices arranged in the passenger compartment;
identifying the number and the position of said one or more occupants seated in the passenger compartment;
determining an optimized tuning by calculating a thermal index at least based on the body temperature detected by the sensor member, body index associated with the one or more occupants, and a metabolic index; and
controlling the ventilation devices as a function of the optimized tuning;
wherein the optimized tuning changes depending on the metabolic index associated with a driving style determined based on data detected by means of an inertial measuring unit, and the body index of the occupant, wherein the driving style is determined based on longitudinal acceleration, lateral or transverse acceleration, and speed of the road vehicle, wherein the metabolic index is estimated in real time for each occupant based on the detected inertial data, wherein the optimized tuning is dynamically adjusted to provide individualized thermal comfort for each occupant as a function of both the real-time metabolic index and the body index, and wherein the control of the ventilation devices is performed independently of any adjustment to powertrain or compressor load, and is based solely on optimizing occupant comfort in response to physiological responses to the detected driving style.

2. The control method according to claim 1, wherein the optimized tuning changes upon variation of said at least one body temperature of a part of the body of at least one of the occupants of the passenger compartment.

3. The control method according to claim 1, wherein the optimized tuning changes depending on the build of at least one of the occupants.

4. The control method according to claim 1, wherein the optimized tuning changes depending on a clothing index associated with clothes worn by at least one of the occupants of the passenger compartment.

5. The control method according to claim 4, wherein the clothing index is determined based on a difference between the body temperature of a part of the body covered by the clothes and the body temperature of an uncovered part of the body of at least one of the occupants.

6. The control method according to claim 1, wherein the optimized tuning changes depending on the gender and/or on the temperature of the head of at least one of the occupants.

7. The control method according to claim 1, wherein the optimized tuning changes depending on the irradiation of the road vehicle.

8. The control method according to claim 7, wherein the irradiation of the road vehicle is processed based on a signal detected by an outer irradiation sensor and/or on a difference between a body temperature of a right part and a body temperature of a left part of the body of at least one of the occupants, which are detected using a thermal camera.

9. The control method according to claim 1, wherein the optimized tuning changes based on the temperature on the outside of the passenger compartment; in particular, the temperature on the outside of the passenger compartment is processed based on the temperature of at least one window, which is detected by means of a thermal camera arranged inside the passenger compartment.

10. The control method according to claim 1 and comprising the further steps of:

detecting a temperature on the inside of the passenger compartment by means of at least one thermometer arranged inside the passenger compartment; and refining the optimized tuning based on the inner temperature detected by said at least one thermometer.

11. The control method according to claim 10 and comprising the further steps of:

comparing the temperature on the inside of the passenger compartment with a desired temperature; and refining the optimized tuning based on a difference between the temperature on the inside of the passenger compartment and the desired temperature.

12. The control method according to claim 1 and comprising the further step of adjusting a flow rate and/or a temperature of an air flow flowing out of said plurality of ventilation devices arranged in the passenger compartment.

13. An air conditioning system in a passenger compartment of a road vehicle (1); the air conditioning system comprises:

an interface device to set a desired temperature signal;

a plurality of ventilation devices arranged in the passenger compartment;

a control unit, which is configured to control said plurality of ventilation devices;

at least one sensor member to identify at least the number and the position of the occupants seated in the passenger compartment; and a processing device, which determines an optimized tuning based on the detection of the sensor member by calculating a thermal index at least based on the body temperature detected by the sensor member, body index associated with the one or more occupants, and a metabolic index associated with a driving style for each occupant, wherein the metabolic index is estimated in real time based on data detected by means of an inertial measuring unit and wherein the optimized tuning is dynamically adjusted to provide individualized thermal comfort for each occupant as a function of both the real-time metabolic index and the body index, wherein the data comprises longitudinal acceleration, lateral or transverse acceleration, and speed of the road vehicle, and wherein the control of the ventilation devices is performed independently of any adjustment to powertrain or compressor load, and is based solely on optimizing occupant comfort in response to physiological responses to the detected driving style and controls the ventilation devices based on the optimized tuning.

14. The air conditioning system according to claim 13, wherein the sensor member comprises at least one thermal camera, which is designed to frame one or more occupants of the passenger compartment and to determine the temperature of at least a part of the body of said at least one or more occupants of the passenger compartment.

\* \* \* \* \*